United States Patent [19]

Dugstad et al.

[11] Patent Number: 5,990,263
[45] Date of Patent: Nov. 23, 1999

[54] CONTRAST AGENTS

[75] Inventors: Harald Dugstad, Oslo; Pål Rongved, Nesoddtangen; Roald Skurtveit, Oslo, all of Norway

[73] Assignee: Nycomed Imaging ASA, Norway

[21] Appl. No.: 08/610,257

[22] Filed: Mar. 4, 1996

Related U.S. Application Data

[63] Continuation-in-part of application No. PCT/GB94/01923, Sep. 5, 1994, and application No. PCT/GB95/02109, Sep. 6, 1995.

[30] Foreign Application Priority Data

Sep. 6, 1994 [GB] United Kingdom .................. 9417941

[51] Int. Cl.[6] .................................................. C08G 67/00
[52] U.S. Cl. ........................ 528/271; 528/272; 528/302; 528/307; 528/308; 424/9.3; 424/9.5
[58] Field of Search ................................... 528/271, 272, 528/302, 307, 308; 424/9.3, 9.5

[56] References Cited

U.S. PATENT DOCUMENTS 5,674,468 10/1997 Klaveness et al. ...................... 424/9.3

FOREIGN PATENT DOCUMENTS

| 0 441 468 | 8/1991 | European Pat. Off. . |
|---|---|---|
| 0 458 745 | 11/1991 | European Pat. Off. . |
| 0 535 534 | 4/1993 | European Pat. Off. . |
| 92/04392 | 3/1992 | WIPO . |
| 92/11873 | 7/1992 | WIPO . |
| 92/17212 | 10/1992 | WIPO . |
| 92/17213 | 10/1992 | WIPO . |
| 93/17718 | 9/1993 | WIPO . |
| 93/18070 | 9/1993 | WIPO . |
| 93/25242 | 12/1993 | WIPO . |

*Primary Examiner*—Mark L. Warzel
*Attorney, Agent, or Firm*—Bacon & Thomas PLLC.

[57] ABSTRACT

Novel extended polymer surfactants comprising a methoxy-terminated polyethylene glycol hydrophilic block acylated with a hydrophobic moiety comprising a chain of at least two fatty acid units, e.g. an acyloxyacyl group such as 16-hexadecanoyloxyhexadecanoyl, are useful in the preparation of polymer-based gas-containing contrast agents by emulsion techniques.

6 Claims, No Drawings

CONTRAST AGENTS

This application is a continuation-in-part of pending International Patent Application No. PCT/GB94/01923 filed Sep. 5, 1994 and of pending International Patent Application No. PCT/GB95/02109 filed Sep. 6, 1995.

This invention relates to novel extended polymer surfactants useful in the manufacture of gas-containing contrast agents which are themselves of use in diagnostic imaging.

Block copolymer surfactants include block copolymers having two or more blocks of differing lyophilicity, for example in linear di-block, tri-block or multi-block arrays, e.g. of the type A-B, A-B-A, B-A-B or A-B-A-B-A-B where A and B are polymer blocks of differing lyophilicity, e.g. hydrophilic and hydrophobic blocks respectively. They also include branched structures, e.g. of the type

and macrocyclic structures, e.g. of the type

The size of one or other type of block may if desired be chosen to be relatively small in order to obtain a desired hydrophilic/lipophilic balance. Thus, for example, in the case of block copolymers containing hydrophilic and hydrophobic blocks it may be advantageous to select small-sized hydrophobic blocks in order to render the copolymer water-soluble.

In general where small-sized blocks are present these may include both oligomeric groups and quasi-polymeric groups, including monomeric groups, which may for example exhibit polymer characteristics (e.g. as a result of the presence of long chain units) while not strictly possessing a definable repeating unit. Copolymers containing such oligomeric or quasi-polymeric blocks are sometimes described in the art as "extended polymers".

The present invention concerns surfactants which are extended polymers comprising a methoxy-terminated polyethylene glycol hydrophilic block acylated with a hydrophobic moiety comprising a chain of two or more fatty acids, e.g. straight chain saturated or unsaturated fatty acids, for example containing 10–20 carbon atoms. The hydrophobic moiety may thus, for example, be an acyloxyacyl group such as 16-hexadecanoyloxyhexadecanoyl. Examples of such polymers in accordance with the invention are:

PEG 2300 methyl ether 16-hexadecanoyloxyhexadecanoate;

PEG 5000 methyl ether 16-hexadecanoyloxyhexadecanoate; and

PEG 10000 methyl ether 16-hexadecanoyloxyhexadecanoate.

Such surfactants are useful as emulsifying agents which may be incorporated as additives into contrast agents comprising gas-containing polymer microparticles and/or microballoons wherein the polymer is a biodegradable polymer comprising repeating units of formula (I)

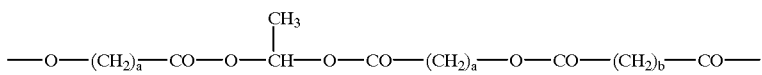

where a represents an integer in the range 9–19, e.g. 13–17, and b represents an integer in the range 1–8, e.g. 3–6). Such contrast agents have been found to exhibit very sharp ultrasound contrast effects in animal tests, for example providing both myocardial contrast enhancement in dogs in all parts of the ventricular wall and excellent contrast enhancement of the kidney. Echogenicity may also be retained following uptake of the contrast agents by the reticuloendothelial system, permitting use as a macrophage imaging agent.

Such contrast agents also exhibit excellent storage stability, for example maintaining their echogenicity in an aqueous suspension for eight weeks at 25° C. They are, however, rapidly degraded and eliminated from the body following administration, e.g. having a half life of 1–2 days in the liver.

The above contrast agents, which may be used in a variety of diagnostic imaging techniques, including ultrasound, MR and X-ray imaging, may incorporate further additives such as other emulsifying agents, as well as coating agents, plasticisers, bulking agents, cryoprotectants and/or antioxidants, for example to modify their stability, dispersibility, aggregation tendencies, biological properties etc., or to modify the flexibility and/or polarity of the polymer membrane.

Contrast agents comprising gas microbubbles encapsulated by a non-polymerisable wall-forming block or graft copolymer surfactant, for example an extended multiblock copolymer from PEG 1500 and ethylidene bis [16-(5-chlorocarbonylpentanoyloxy)hexadecanoate], may if desired incorporate one or more additional emulsifiers, including extended polymers, for example PEG 10000 methyl ether 16-hexadecanoyloxyhexadecanoate.

The extended polymer surfactants of the invention may be used as emulsifiers in the preparation of polymer-based contrast agents by emulsion techniques, e.g. such as are known in the polymer art, the emulsifier conveniently being predissolved in the aqueous phase of the emulsion.

One such preparative method corresponds to the interfacial deposition techniques described in EP-A-0398935 and EP-A-0458745 and comprises dissolving or suspending the polymer in a water-immiscible organic solvent, emulsifying (e.g. by high speed stirring or high shear mixing) the resulting solution or suspension in an aqueous phase in the presence of the surfactant, which stabilises the resulting oil-in-water emulsion, and subsequently removing at least the organic phase, preferably both phases (e.g. by evaporation or lyophilisation, preferably under an atmosphere of the gas which is to be incorporated, e.g. under reduced pressure) whereby the polymer forms a membrane at the interface between the aqueous and organic phases.

Organic solvents useful in such processes include aliphatic, cycloaliphatic and araliphatic hydrocarbons, e.g. containing up to 10 carbon atoms, for example n-octane, cyclooctane, cyclohexane, a dimethylcyclohexane, ethylcyclohexane, a methylheptane, an ethylhexane, toluene, xylene or a terpene, terpenoid or isoprenoid such as camphene or limonene; haloalkanes, such as dichloromethane, chloroform, carbon tetrachloride, methyl bromide or a Freon; esters, such as ethyl or propyl acetate, butyl formate or propyl or isopropyl butyrate or isobutyrate; and appropriate ethers and other lipophilic solvents. Solvents such as camphene are of advantage in that they are biotolerated, so that it is not necessary to remove all solvent residues from the contrast agent prior to administration. Such high-melting solvents may also be advantageous in processes in which the emulsion is frozen and lyophilised, since they will rapidly solidify under these conditions and so may enhance the structural integrity of the resulting microparticulate contrast agent.

The following non-limitative Examples serve to illustrate the invention.

EXAMPLE 1—PREPARATION OF INTERMEDIATES AND POLYMERS a) Ethylidene bis(16-hydroxyhexadecanoate)

1,8-Diazabicyclo [5.4.0]undec-7-ene (1,5-5) (DBU) (2.74 g, 0.018 mol) was added to 16-hydroxyhexadecanoic acid (4.90 g, 0.018 mol) in dimethylformamide (150 ml). After 5 minutes with stirring, ethylidene iodide (2.54 g, 0.009 mol) was added and the mixture was left with stirring at 40° C. for 3 days. The reaction mixture was cooled to 20° C. and when precipitation was complete (2 hours) the precipitated monomer was isolated by filtration. The monomer was treated with activated carbon and recrystallised twice from dichloromethane to give 1.03 g (20%) of the title product. Differential scanning calorimetry (DSC) indicated that onset melting temperature was 88.93° C. $^1$H NMR (200 MHz, CDCl$_3$): δ 1.25 (s, 44H, CH$_2$), 1.45 (d, 3H, C$\underline{H}_3$CH), 1.56 (m, 8H, CH$_2$), 2.30 (t, 4H, CH$_2$CO), 3.63 (t, 4H, 2 X CH$_2$O), 6.86 (q, 1H, C$\underline{H}$CH$_3$). $^{13}$C NMR (50 MHz, CDCl$_3$): δ 20.86, 25.91, 26.98, 30.22, 30.44, 30.67, 30.84, 34.00, 35.30, 64.00, 89.00, 171.77 (C=O).

b) Ethylidene bis[16-(5-chlorocarbonylpentanoyloxy)-hexadecanoate]

In a three-necked round bottomed flask equipped with a reflux condenser, a glass gas inlet tube and a pressure equalizing dropping funnel was placed freshly distilled adipoyl chloride (2.60 ml, 17.50 mmol) dissolved in absolute chloroform (15 ml). The temperature was raised to ca. 50° C. and under a gentle stream of nitrogen through the solution, a solution of ethylidene bis(16-hydroxyhexadecanoate) (1.0 g, 1.75 mmol) in absolute chloroform (30 ml) was added dropwise and left at this temperature a further 3 hours after addition. The mixture was then cooled to room temperature and quickly transferred into a 50 ml round bottomed flask equipped for distillation under reduced pressure. Chloroform was first distilled off at normal pressure, then oil-pump vacuum was established and excess adipoyl chloride distilled off at ca. 75° C., 5 mbar pressure, leaving the residual title compound (1.56 g).

c) 16-Hexadecanoyloxyhexadecanoic acid

16-Hydroxyhexadecanoic acid (5.43 g, 19.9 mmol) was dissolved in tetrahydrofuran (190 ml) and pyridine (2.36 g, 29.9 mmol) was added. Palmitoyl chloride (5.48 g, 19.9 mmol) was dissolved in tetrahydrofuran (10 ml) and added dropwise at room temperature. After stirring at room temperature for 16 hours, the mixture was filtered and the filtrate evaporated under reduced pressure. The residue was dissolved in chloroform, washed with water (3×50 ml), and the organic phase was dried (MgSO$_4$). After evaporating under reduced pressure, the residue was purified on a silica column, eluting with chloroform with increasing methanol concentration (from 1% to 2% methanol in chloroform) to give 8.41 g (83%) of the title compound. $^1$H NMR (300 MHz, CDCl$_3$): δ 0.85 (t, 3H, CH$_3$), 1.20–1.35 (s, 46H, —CH$_2$—), 1.55–1.70 (m, 6H, —CH$_2$—), 2.25 (t, 2H, —CH$_2$—C(O)—O), 2.45 (t, 2H, —C$\underline{H}_2$—COOH), 4.05 (t, 2H, —O—CH$_2$). $^{13}$C NMR (75 MHz, CDCl$_3$): δ 14.01, 22.57, 24.10, 24.91, 25.82, 28.53, 28.75, 28.94, 29.08, 29.15, 29.25, 29.36, 29.54, 31.81, 34.29, 35.16, 64.27, 76.48, 76.90, 77.10, 77.32, 169.50, 173.91.

d) 16-Hexadecanoyloxyhexadecanoyl chloride

16-Hexadecanoyloxyhexadecanoic acid (7.73 g, 15.13 mmol) prepared as in (c) above was dissolved in tetrahydrofuran (140 ml) and oxalyl chloride (4.80 g, 37.83 mmol) was added dropwise. The mixture was stirred at room temperature for 3 days and then the solvent and unreacted oxalyl chloride were evaporated under reduced pressure to give 8.0 g (100%) of the title compound.

e) Preparation of Methoxy-endcapped polyethylene glycols (PEGs)

Preparation of a Typical Polymer (MeO-PEG 2000)

An initiator solution was prepared by careful addition of potassium metal (0.400 g, 10.23 mmol) to methanol (1.300 g, 40.57 mmol) in an inert atmosphere. A portion of this initiator solution (0.220 g, 1.32 mmol potassium methoxide) was injected into an ampoule containing ethylene oxide (10.000 g, 227.00 mmol). The sealed ampoule was allowed to stand at room temperature overnight. The temperature was then raised to 60° C. and reaction allowed for 72 hours. After removal of unreacted monomer, the contents of the ampoule were dissolved in dichloromethane and the solution neutralised with dilute aqueous hydrochloric acid. The polymer solution was washed three times with distilled water, rotary evaporated and then vacuum dried. Assignments for MeO-PEG polymers. $^1$H-NMR: δ 2.7 (OH), 3.2 (OCH$_3$), 3.5 (—CH$_2$—main chain), 3.4 (—C$\underline{H}_2$OCH$_3$). $^{13}$NMR: δ 58.5 (—OCH$_3$), 61.2 (—CH$_2$OH), 70.5 (—C$\underline{H}_2$—main chain), 71.3 (—CH$_2$OCH$_3$), 72.2 (—C$\underline{H}_2$CH$_2$OH). Gas phase chromatography (GPC) was performed in tetrahydrofuran, with molecular weight calibration via PEG standards. GPC data for a typical sample: molecular weight at maximum detector response: 2679, number average molecular weight: 2012, weight average molecular weight: 2283. Polydispersity: 1.135.

f) Polymer from ethylidene bis(16-hydroxyhexadecanoate) and adipoyl chloride

A solution of adipoyl chloride (0.48 g, 2.6 mmol) in xylene/trichloroethylene (80:20 v/v, 5 ml) was added to a solution of ethylidene bis(16-hydroxyhexadecanoate) (1.48 g, 2.6 mmol) from Example 1(a) above in xylene/trichloroethylene (80:20 v/v, 100 ml) at 60° C. After 2 days at 60° C. under reduced pressure (147 mbar), the reaction mixture was cooled to 20° C. The solvent was evaporated under reduced pressure, the resulting polymer was dissolved in chloroform, reprecipitated in hexane and filtered, giving 1.05 g (60%) of the title compound as a white powder. Size Exclusion Chromatography (SEC): weight average molecular weight: 39068, number average molecular weight: 9442, molecular weight at maximum detector response 48536, polydispersity: 4.138 (using polystyrene as standards). Differential scanning calorimetry (DSC) indicated that onset melting temperature was 48.61° C. $^1$H NMR (200 MHz, CDCl$_3$): δ 1.28 (s, 44H, CH$_2$), 1.45 (d, 3H, C$\underline{H}_3$CH), 1.62 (m, 12H, CH$_2$), 2.32 (m, 8H, CH$_2$CO), 4.02 (t, 4H, 2 X CH$_2$O), 6.88 (q, 1H, C$\underline{H}$CH$_3$). $^{13}$C NMR (50 MHz, CDCl$_3$): δ 20.85, 25.64, 25.68, 25.89, 27.16, 29.84, 30.15, 30.21, 30.44, 30.81, 35.08, 35.12, 35.27, 65.45, 88.98, 171.77 (C=O), 173.41 (C=O).

g) Extended polymer from PEG 1500 and ethylidene bis [16-(5-chlorocarbonylpentanoyloxy)hexadecanoate] (multiblock)

Ethylidene bis[16-(5-chlorocarbonylpentanoyloxy) hexadecanoate] prepared as in Example 1(b) (1.02 g, 1.18 mmol) was dissolved in toluene (20 ml) in a 100 ml 3-necked round bottomed flask equipped with a glass gas inlet tube and a reflux condenser. PEG 1500 (1.77 g, 1.18 mmol) was added and the mixture heated at 60° C. for 22 hours, cooled to room temperature and the solvent removed under reduced pressure to give the title compound (2.29 g) as a white wax.

EXAMPLE 2 —PREPARATION OF EMUSIFIERS a) PEG 2300 methyl ether 16-hexadecanoyloxyhexadecanoate PEG 2300 methyl ether (10.000 g, 4.35 mmol) was dissolved in tetrahydrofuran (90 ml) and pyridine (0.413 g, 5.22 mmol) was added. 16-Hexadecanoyloxyhexadecanoyl chloride (2.301 g, 4.35 mmol) was dissolved in tetrahydrofuran (10 ml) and added dropwise. After stirring for 3 days at room temperature, the mixture was filtered and the solvent was evaporated under reduced pressure. The residue (12.08 g) was purified on a silica column, eluting with chloroform with increasing methanol concentration (from 1% to 3% methanol in chloroform) to give 5.20 g (43%) of the title compound. $^1$H NMR (300 MHz, CDCl$_3$): δ b 0.80–0.87 (m, CH$_3$), 1.21 (s, (br), CH$_2$), 1.53–1.62 (m, CH$_2$), 2.20–2.35 (m, CH$_2$CO), 3.34 (s, CH$_3$O), 3.61 (s, OCH$_2$CH$_2$O), 4.02 (t, COOCH$_2$CH$_2$O), 4.19 (t, COOCH$_2$CH$_2$O). $^{13}$C NMR (75 MHz, CDCl$_3$): δ 13.95, 22.49, 24.71, 24.83, 25.74, 28.45, 28.95, 29.07, 29.16, 29.28, 29.34, 29.40, 29.46, 31.72, 34.05, 34.21, 58.85, 63.15, 64.19, 69.01, 70.37, 71.73, 173.64, 173.82.

b) PEG 5000 methyl ether 16-hexadecanoyloxyhexadecanoate)

PEG 5000 methyl ether (7.500 g, 1.50 mmol) was dissolved in toluene (90 ml) and dried by refluxing in a Dean Stark apparatus. Pyridine (0.143 g, 1.80 mmol) was added followed by addition (dropwise) of 16-hexadecanoyloxy-hexadecanoyl chloride (1.191 g, 2.25 mmol) dissolved in toluene (10 ml). The mixture was heated to reflux and after stirring under reflux for 3 days the mixture was cooled to room temperature and precipitated into hexane. After filtering, the precipitate was washed with hexane and dried (MgSO$_4$). After evaporation under reduced pressure, the residue was purified on a silica column, eluting with chloroform with increasing methanol concentration (from 1% to 3% methanol in chloroform) to give 5.93 g (72%) of the title compound. $^1$H NMR (300 MHz, CDCl$_3$): δ 0.82–0.86 (m, CH$_3$), 1.22 (s, (br), CH$_2$), 1.53–1.62 (m, CH$_2$), 2.20–2.35 (m, CH$_2$CO), 3.34 (s, CH$_3$O), 3.61 (s, OCH$_2$CH$_2$O), 4.01 (t, COOCH$_2$CH$_2$O), 4.18 (t, COOCH$_2$O). $^{13}$C NMR (75 MHz, CDCl$_3$): δ 13.66, 22.21, 24.43, 24.54, 25.46, 28.17, 28.67, 28.79, 28.87, 28.99, 29.06, 29.11, 29.17, 31.44, 33.73, 33.93, 58.57, 62.87, 63.90, 68.72, 69.62, 69.86, 70.09, 71.45, 76.85, 173.35, 173.53.

c) PEG 10000 methyl ether 16-hexadecanoyloxyhexadecanoate

PEG 10000 methyl ether (7.500 g, 0.75 mmol) was dissolved in toluene (140 ml) and pyridine (0.107 g, 1.35 mmol) was added. The solution was heated to 60° C. and 16-hexadecanoyloxyhexadecanoyl chloride (0.595 g, 1.12 mmol) dissolved in toluene (10 ml) was added dropwise. The mixture was heated to reflux and after stirring under reflux for 3 days the mixture was cooled to room temperature and precipitated into hexane. After filtering, the precipitate was washed with hexane and dried. Flash chromatography on a silica column, eluting with 5% methanol in chloroform, gave 5.39 g (68%) of the title compound. $^1$H NMR (300 MHz, CDCl$_3$): δ 0.84 (t, CH$_3$), 1.21 (s, (br), CH$_2$), 1.55–1.60 (m, CH$_2$), 2.20–2.35 (m, CH$_2$CO), 3.34 (s, CH$_3$O), 3.61(s, OCH$_2$CH$_2$O), 4.01 (t, COOCH$_2$CH$_2$O), 4.18 (t, COOCH$_2$CH$_2$O). $^{13}$C NMR (75 MHz, CDCl$_3$): δ 13.94, 22.48, 24.70, 24.82, 25.73, 28.94, 29.05, 29.14, 29.26, 29.33, 29.39, 29.45, 31.71, 34.00, 58.84, 63.14, 68.99, 69.36, 69.86, 69.97, 70.01, 70.36, 70.74, 70.82, 70.86, 71.72, 77.10, 173.62, 173.80.

EXAMPLE 3 —USE OF EMULSIFIERS IN PREPARATION OF POLYMER PARTICLES a) Particles from polymer made from ethylidene bis(16-hydroxyhexadecanoate) and adipoyl chloride 10 ml of a 5 w/v solution of the polymer from Example 1(f) in (-)-camphene maintained at 60° C. were added to 30 ml of a 1 w/w aqueous solution of PEG 5000 methyl ether 16-hexadecanoyloxyhexadecanoate from Example 2(b) above at the same temperature. The mixture was mixed with a rotor-stator mixer (Ultra Turax® T25) at slow speed for several minutes, frozen on a dry ice/methanol bath, and lyophilized for 48 hours, giving a white powder.

b) Particles from polymer made from ethylidene bis(16-hydroxyhexadecanoate) and adipoyl chloride 10 ml of a 5% w/v solution of the polymer from Example 1(f) in (-)-camphene maintained at 60° C. were added to 30 ml of a 1% w/w aqueous solution of PEG 10000 methyl ether 16-hexadecanoyloxyhexadecanoate from Example 2(c) above at the same temperature. The mixture was mixed with a rotor-stator mixer (Ultra Turax® T25) at slow speed for several minutes, frozen on a dry ice/methanol bath, and lyophilized for 48 hours, giving a white powder.

c) Particles from polymer made from ethylidene bis(16-hydroxyhexadecanoate) and adipoyl chloride 16 ml of a 3% w/v solution of the polymer from Example 1(f) in (-)-camphene maintained at 70° C. was added to 64 ml of an aqueous solution containing 1% w/v of PEG 10000 methyl ether 16-hexadecanoyloxyhexadecanoate from Example 2(c) and 5% w/v of PEG 3000 at the same temperature. The mixture was mixed with a rotor-stator mixer at moderate speed for up to 5 minutes, frozen on a dry ice/methanol bath, and lyophilized for 48 hours, giving a white powder. The dry product was dispersed in saline solution on a laboratory shaker for 16 hours at a concentration of 10 mg dry material/ml.

d) Particles from polymer made from ethylidene bis(16-hydroxyhexadecanoate) and adipoyl chloride The procedure of Example 3(c) was repeated, but with cyclooctane in place of (-)-camphene as organic solvent.

e) Particles from polymer made from ethylidene bis(16-hydroxyhexadecanoate) and adipoyl chloride The procedure of Example 3(c) was repeated, but with cyclohexane in place of (-)-camphene as organic solvent.

f) Particles from polymer made from ethylidene bis(16-hydroxyhexadecanoate) and adipoyl chloride The procedure of Example 3(c) was repeated, except that emulsification was carried out at 60° C. using 28 ml of a 7.5% w/v solution of the polymer from Example 1(f) in (-)-camphene and 62 ml of an aqueous solution containing 2% w/v of PEG 10000 methyl ether 16-hexadecanoyloxyhexadecanoate from Example 2(c).

g) Preparation of microbubbles of extended polymers from Examples 1(g) and 2(c) filled with perfluoro-n-butane Polymer from Example 1(g) (0.01 g) was dissolved in distilled water (0.5 ml) and added to 0.5 ml of an aqueous solution (1%) of PEG 10000 methyl ether 16-hexadecanoyloxyhexadecanoate from Example 2(c). The solution was degassed, and the headspace of the vessel was filled with perfluoro-n-butane and shaken for 99 seconds on a Capmix®. Perfluoro-n-butane-filled microbubbles of a size suitable for intravenous administration were observed in a microscope. The microbubbles were stable for several days.

EXAMPLE 4 —ACOUSTIC CHARACTERIZATIONS.

General Procedure

Dry powders of polymer particles prepared according to Example 3 (a) and (b) above were redispersed to 10 mg/ml dry material in MilliQ water by shaking on a laboratory shaker for 12–16 hours. Examination by light microscopy indicated formation of particle dispersions. The particles floated readily, as expected for gas-containing particles.

Acoustic effects in vitro

The acoustic effect of suspensions prepared as above was obtained by measuring the ultrasonic transmission through solutions of different concentrations (mg/ml) in an aqueous carrier liquid, using a 3.5 MHz broadband transducer in a pulse-reflection technique. The aqueous carrier liquid was used as reference, and measurements were performed on serial dilutions with the carrier liquid until the signal was reduced to approximiately 3–5 db/cm. The concentration necessary to give an attenuation of 8 db/cm was noted (Table 1); hence low values indicate a good contrast effect. The obtained acoustic effects are at a level indicating that the products can be expected to be useful as ultrasound contrast agents. According to theoretical considerations, solid (as opposite to gas-containing) particles of the same size and at the same dilutions should give an acoustic attenuation of less than 0.1 db/cm.

TABLE 1

Acoustic measurements of particles from Example 3 (a) and (b) above. The acoustic measurements are given in column 3 as the concentration giving a contrast effect of 8 db/cm, i.e half value of saturated signal. At higher concentrations, the signal intensity increased until saturation was observed.

TABLE 1

Acoustic measurements of particles from Example 3 (a) and (b) above. The acoustic measurements are given in column 3 as the concentration giving a contrast effect of 8 db/cm, i.e half value of saturated signal. At higher concentrations, the signal intensity increased until saturation was observed.

| Example 4 | Particles of Example | Particle conc. at 8 db/cm [mg/ml] |
|---|---|---|
| a | 3a | 0.03 |
| b | 3b | 0.01 |

We claim:

1. A surfactant comprising a mono-(methoxy-terminated) polyethylene glycol hydrophilic block acylated at the other terminus thereof with a hydrophobic chain moiety comprising an acyloxyacyl group wherein the acyl portions derive from straight chain saturated or unsaturated fatty acids containing 10–20 carbon atoms.

2. The surfactant of claim 1 wherein the acyloxyacyl group is 16-hexadecanoyloxyhexadecanoyl.

3. A surfactant coating on a contrast-enhancing microparticle, which surfactant comprises a mono-(methoxy-terminated) polyethylene glycol hydrophilic block acylated at the other terminus thereof with a hydrophobic chain moiety comprising an acyloxyacyl group wherein the acyl portions derive from straight chain saturated or unsaturated fatty acids containing 10–20 carbon atoms.

4. The surfactant of claim 2 which is a methyl ether 16-hexadecanoyloxyhexadecanoate and wherein the polyethylene glycol hydrophilic block has a weight average molecular weight of about 2300.

5. The surfactant of claim 2 which is a methyl ether 16-hexadecanoyloxyhexadecanoate and wherein the polyethylene glycol hydrophilic block has a weight average molecular weight of about 5000.

6. The surfactant of claim 2 which is a methyl ether 16-hexadecanoyloxyhexadecanoate and wherein the polyethylene glycol hydrophilic block has a weight average molecular weight of about 10000.

* * * * *